US007015313B2

United States Patent
Kim et al.

(10) Patent No.: US 7,015,313 B2
(45) Date of Patent: Mar. 21, 2006

(54) LECTIN PROTEIN PREPARED FROM KOREAN MARINE CRAB *PHILYRA PISUM*, PROCESS FOR PREPARING THE SAME AND THE USE THEREOF

(75) Inventors: Ha-Hyung Kim, Ma-1008 Bangbaesamho Apt., 725 Bangbae-dong, Seocho-ku, Seoul (KR), 137 060; Jai-Il Jun, Anyang-si (KR); Bum-Soo Kim, Seoul (KR); Due-Hyeon Cho, Seongnam-si (KR); Tae-Hong Min, Seongnam-si (KR); Yun-Jung Kim, Kwangmyong-si (KR); Chang-Soo Ryu, Seoul (KR)

(73) Assignee: Ha-Hyung Kim, Seoul (KR)

( * ) Notice: Subject to any disclaimer, the term of this patent is extended or adjusted under 35 U.S.C. 154(b) by 0 days.

(21) Appl. No.: 10/476,904

(22) PCT Filed: May 4, 2002

(86) PCT No.: PCT/KR02/00828

§ 371 (c)(1),
(2), (4) Date: Apr. 29, 2004

(87) PCT Pub. No.: WO02/090376

PCT Pub. Date: Nov. 14, 2002

(65) Prior Publication Data

US 2004/0185428 A1 Sep. 23, 2004

(30) Foreign Application Priority Data

May 4, 2001 (KR) .......................... 2001-24330

(51) Int. Cl.
*C07K 1/00* (2006.01)
*C07K 14/00* (2006.01)
*C07K 17/00* (2006.01)

(52) U.S. Cl. ............................. 530/396; 530/350; 435/4
(58) Field of Classification Search ................. 530/350, 530/396; 435/4
See application file for complete search history.

(56) References Cited

PUBLICATIONS

Mercy et al., Purification and characterization of N–glyco-lyneuraminic–acid–specific lectin from Scylla serrata. Eur J Biochem. Aug. 1, 1993;215(3):697–704.*

* cited by examiner

*Primary Examiner*—Jon Weber
*Assistant Examiner*—Robert B. Mondesi
(74) *Attorney, Agent, or Firm*—Duane Morris LLP

(57) ABSTRACT

The present invention relates to a lectin protein prepared from Korean marine crab *Philyra pisum*, process for preparing the same and the use thereof. This protein can be used as a diagnosing agent or a carrier protein that chemically binds to various anti-cancer drugs owing to its capability that specifically recognizes N-glycolylneuraminic acid, and, in addition, used as an anti-cancer drug in view of its anti-proliferation effect.

11 Claims, 3 Drawing Sheets

SEQUENCE LISTING

```
<160> NUMBER OF SEQ ID NOS: 1

<210> SEQ ID NO 1
<211> LENGTH: 10
<212> TYPE: PRT
<213> ORGANISM: Philyra pisum
<220> FEATURE:
<221> NAME/KEY: PEPTIDE
<222> LOCATION: (1)..(9)
<223> OTHER INFORMATION: N-Terminal

<400> SEQUENCE: 1

Ile Val Gly Gly Thr Glu Ala Thr Pro His
1               5                   10
```

LECTIN PROTEIN PREPARED FROM KOREAN MARINE CRAB *PHILYRA PISUM*, PROCESS FOR PREPARING THE SAME AND THE USE THEREOF

CROSS-REFERENCES TO RELATED APPLICATIONS

This application is a 371 of co-pending PCT Application No. PCT/KRO2/00828 filed 4 May 2002, which is now inactive, and is entitled to priority pursuant to 35 U.S.C. §120 to Republic of Korea patent application 2001-0024330, which was filed on 4 May 2001.

BACKGROUND OF THE INVENTION

The present invention relates to a lectin protein isolated from the Korean marine crab, *Philyra pisum* in the family Leucosiidae, a process for preparing the same and the use thereof. More specifically, the present invention relates to a lectin designated PPA (*Philyra pisum* agglutinin) that is a protein component isolated from the hemolymph of Korean marine crab *Philyra pisum* and specifically binds to N-glycolylneuraminic acid, a process for isolating and purifying the same, and the various uses of the PPA based on its biological activities.

In general, differentiation and growth as intercellular recognition and interaction processes in a normal living body not affected by a disease are considered as essential processes. Abnormality occurring in differentiation and growth may causes incomplete development, malformation or cancer in cells. With recent understanding at the gene and protein levels, carbohydrates on the cell membrane surface have lately been given great attention as a substance that enables the understanding of the vital phenomenon at the molecular level. As an example thereof, it is reported that structural change of carbohydrate on the cell membrane surface is observed in the process of malignant degeneration of animal cells by viruses and the like, and that the abnormality of carbohydrates on the cell membrane commonly occurs in most of cancer cells. A dramatic change of carbohydrate structure has also been reported in development and differentiation processes.

Intercellular recognition occurs by way of carbohydrates on the cell membrane surface. In order to mediate this process, molecules specifically recognizing the carbohydrates should exist on the cell membrane surface. For example, a carbohydrate-binding protein such as lectin is necessary on the cell membrane surface.

*Philyra pisum*, which belongs to the family of Leucosiidae, is distributed throughout the mud areas of the west coast in Korea and characterized by a habit of walking forward unlike the other crabs, and is slow and feigns death when touched. *Philyra pisum* has not been used for food, and thus, biochemical research thereon is very poor.

BRIEF SUMMARY OF THE INVENTION

The present inventors have extensively studied in order to characterize and test biological activity of a glycoprotein lectin designated *Philyra pisum* agglutinin (PPA) the presence of which has not been known hitherto. This was achieved by isolating PPA from the hemolymph of Korean marine crab *Philyra pisum* by a method which will be described below. As a result, the inventors found that PPA has various beneficial biochemical characteristics such as a specific binding to N-glycolylneuraminic acid and thus can be used as diagnostics for various diseases including cancers, an anti-proliferation agent against cancer cells and a carrier protein for treating diseases.

It is therefore an object of the present invention to provide a lectin protein which was isolated from the hemolymph of Korean marine crab *Philyra pisum* and is a kind of proteins which specifically recognize N-glycolylneuraminic acid.

It is another object of the present invention to provide a process for preparing the lectin PPA.

It is further object of the present invention to provide diagnostics for a disease in which the structure of carbohydrates within the cells is modified to N-glycolylneuraminic acid that does not exist in a normal living body, the diagnostics comprising the lectin PPA.

It is still another object of the present invention to provide a use of the lectin PPA as an anti-cancer drug with an anti-proliferation effect on cancer cells.

It is still further object of the present invention to provide a drug conjugate in which the lectin PPA is used as a carrier protein for local transport of a drug or an active agent (for example, an anti-cancer-drug), to form a drug conjugate which selectively binds to a specific cancer cell.

BRIEF SUMMARY OF THE SEVERAL VIEWS OF THE DRAWINGS

Further objects and advantages of the invention can be more fully understood from the following detailed description taken in conjunction with the accompanying drawings in which.

DETAILED DESCRIPTION OF THE INVENTION

Figure 1:
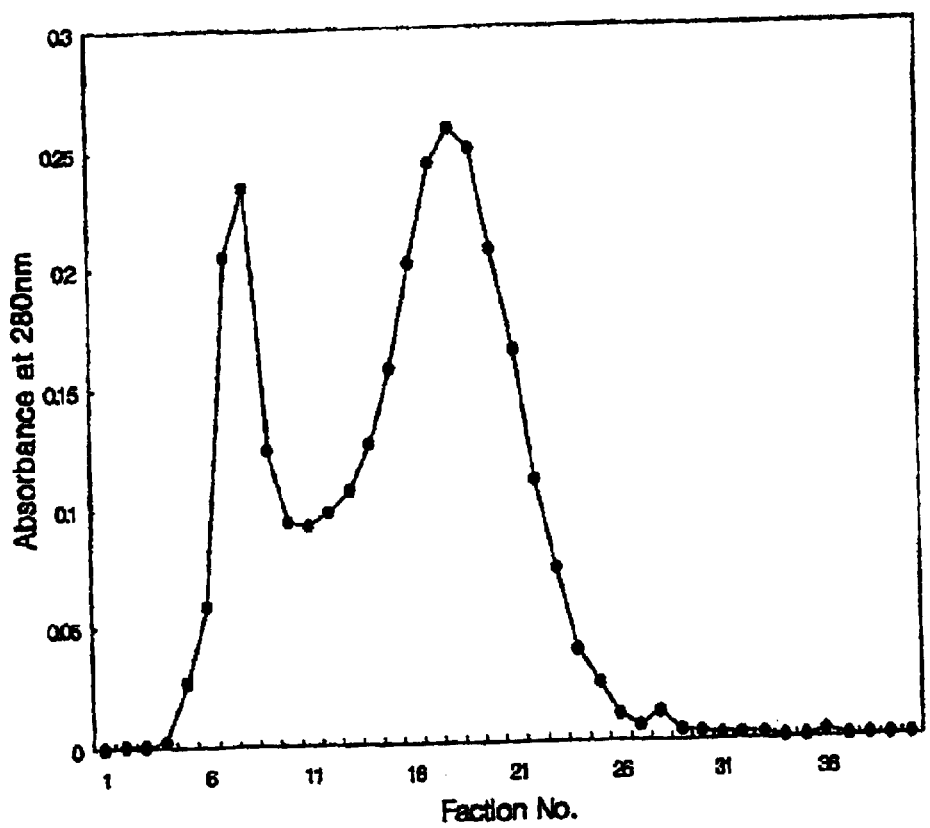
FIG. 1 is a graph showing a UV (280 nm) spectroscopic chromatogram of the lectin PPA prepared by the present invention.

Hereinafter, the present invention will be described in further detail.

Lectins, which are proteins that selectively bind to carbohydrates, have been discovered in plants, microorganisms, virus, invertebrates, and vertebrates, and are widely used as a material in research related to various diseases. Lectin has various functions: it has been known to agglutinate erythrocytes and sediment them, and has been used in determining blood type. In addition, lectin has recently been known to have a function of specifically agglutinating cancer cells. Namely, lectin binds to a carbohydrate with a specific structure and thus enables selective communication between the cells bearing the lectin substance and the cells bearing a carbohydrate which binds to it.

Since the reports on the structural change of carbohydrate of proteins within the living body upon development of rheumatism, cancer or AIDS, there have been attempts to explain the results of these diseases in view of the structural changes of carbohydrate. Especially, it is considered that the remarkable change of sialyl epitopes in the sialoglycoconjugate of the surface of pathogenic or tumor cells results from change in the kind of sialic acid in the oligosaccharides or the carbohydrate binding pattern with the adjacent carbohydrates. Therefore, lectins specifically recognizing various sialic acids and their carbohydrate binding patterns can be used as a tool for identifying various sialyl epitopes in biopsy of pathogens or malignant tumors.

Sialic acid refers to about 30 compounds including N-acetylneuraminic acid or its derivatives such as N-glycolylneuraminic acid, which has an acyl substituent at the C-5 amino group. Most of the other sialic acids have O-acetyl substituent(s) of one or more C-4, C-7, C-8 or C-9 hydroxyl groups. The thus-substituted sialic acids may cause transformation or other changes in the cellular environment and such changes have been known to inhibit or weaken the sialic acid hydrolase of bacteria or viruses to change their immunity, thus affecting enzyme activity relating to catabolism of complex carbohydrates.

In particular, the antibody against the sialyl $Le^a$ sugar shows an 80 to 90% positive response in pancreatic cancer, and the antibody against the sialyl $Le^x$ sugar shows a positive response in gastrointestinal cancers. However, these responses are not caused by appearance of a new sugar due to carcinogenesis, but by changes in the sugar synthetic pathway that change its ratio. Meanwhile, it was reported that sialic acids are converted to N-glycolylneuranminic acid upon disease development, for example, in the case of breast cancer, melanoma or colon cancer, and to an O-acetyl substituent in the case of ovarian cancer or melanoma (See Carr A et al., Hybridoma 19, pp. 241–247, (2000); and Marquina G et al., Cancer Res 56, pp. 5165–5171, (1996)). This research results suggest that lectins which specifically recognize carbohydrates are important for understanding intercellular communications mediated by molecular recognition, and that lectins may also be an important material in the development of diagnosing agents for a specific cancer or a specific therapeutic agent formed by conjugation with drugs such as anti-cancer agents.

Most of the known lectins are reported to specifically recognize D-mannose and D-galactose. Few lectins specifically recognize the non-reduced oligosaccharide terminus of sialic acids that play important structural and functional roles. Moreover, lectins available in large amounts are extremely limited. Sialic acid-binding lectins are mainly found in invertebrate animals, and the isolated lectins are known to specifically recognize a part of or the entire oligosaccharide, similar to the lectins isolated from other sources such as plants. It was reported that mollusks and arthropods produce lectins specific to sialic acids, and that crustaceans cannot synthesize sialic acids but produce sialic acid-binding lectins as the protecting means against bacteria which express various sialoglycoconjugates.

The present invention has been accomplished by conducting various experiments with the Korean marine crab *Philyra pisum* in order to find out a useful material from the living things in nature.

Therefore, the present invention in one aspect provides a lectin PPA which is a kind of protein specifically recognizing N-glycolylneuraminic acid, the PPA being isolated from the hemolymph of the Korean marine crab *Philyra pisum*.

The above lectin component is a single subunit having a molecular weight of 28.9 kDa and its N-terminal amino acid sequence is represented in SEQ ID NO: 1 of the sequence listing. This lectin component was proven to bind N-glycolylneuraminic acid or a glycoprotein containing N-glycolylneuraminic acid by hemagglutination reaction, hemagglutination-inhibition reaction or enzyme-linked immunosorbent assay (ELISA).

The present invention in another aspect provides a process for preparing the lectin PPA from the Korean marine crab *Philyra pisum*.

Specifically, the lectin PPA can be prepared by adding an aqueous 0.15 M NaCl solution to the hemolymph of Korean marine crab *Philyra pisum* while stirring, filtering the precipitation off, isolating a supernatant by centrifugation for 5 hours at 4° C. at 100,000×g and subjecting the supernatant to SEPHADEX (TM) G-25 or analogous gel filtration column chromatography to isolate the protein component.

In addition to the above method, the lectin PPA can be isolated using an affinity column in which a hemagglutination-inhibiting substance (such as bovine submaxillary mucin and tyroglobulin, etc.) is bound to an affinity column substrate material such as CNBr-activated SEPHAROSE (TM) 4B as will be described in detail in Example 5.

The present invention, in a further aspect, provides the use of the lectin PPA as a diagnostic agent for a disease in which the structure of carbohydrates within the cells is modified to N-glycolylneuraminic acid that does not exist in the normal body. The agent comprises the lectin PPA. The examples of the disease may include, but are not limited to, breast cancer, melanoma or colon cancer.

As result of testing biological activity of the PPA, the lectin PPA was shown to specifically bind to N-glycolylneuraminic acid as a monosaccharide and to bovine submaxillary mucin or thyroglobulin containing N-glycolylneuraminic acid as a glycoprotein. Therefore, the lectin PPA can be used as a diagnostic agent based on the principle that it specifically recognizes N-glycolylneuraminic acid which is not present on normal cells but is specifically expressed on breast cancer, melanoma or colon cancer cells.

The present invention, in a still further aspect, provides an anti-proliferation agent which comprises the lectin PPA as an active component.

The lectin PPA according to the present invention can be used as a diagnostic agent or a carrier protein since it selectively recognizes and binds to N-glycolylneuraminic acid or a glycoprotein containing N-glycolylneuraminic acid, as demonstrated by the hemagglutination reaction, hemagglutination-inhibition reaction or ELISA. In addition, the lectin PPA itself has an anti-cancer effect as shown in the test examples which will be described in detail. Therefore, the lectin PPA of the invention can also be used as an active component of an anti-proliferation agent against cancer cells (or an anti-cancer agent) in diseases in which N-glucolylneuraminic acid occurs. Examples of the diseases may include, but are not limited to, hepatoma, bladder cancer, lung cancer, stomach cancer and colon cancer.

The pharmaceutical composition of the anti-proliferation agent against cancer cells according to the present invention can be prepared in combination with the conventional pharmaceutically acceptable carrier. Generally, the active component is mixed with a pharmaceutically acceptable liquid or solid carrier. If necessary, additives such as solvent, dispersant, emulsifier, buffer, stabilizer, diluent, binder, disintegrant, lubricant, etc. can be used. The composition may be in the form of solid formulations such as tablet, granule, powder or capsule, or liquid formulations such as normal liquid, suspension or oil. These formulations may also be made as dry preparations which can be used in the liquid form by addition of a proper carrier before use.

The pharmaceutical composition of the present invention can be administered orally or parenterally, i.e., by way of injection or drop means.

The pharmaceutically acceptable carriers may be selected according to the mode of administration and formulation. In case of oral formulations, for example, the carriers include starch, lactose, refined sugar, mannose, carboxymethylcellulose, corn starch, or inorganic salts. In the preparation of oral formulations, binder, disintegrant, surfactant, lubricant, fluidity enhancer, sweetening agent, coloring agent or flavor can be additionally used.

The parenteral formulation is prepared by dissolving or suspending the composition containing the lectin PPA as the active component of the present invention in a diluent, such as distilled water for injection, physiological salt solution, aqueous glucose solution, vegetable oil for injection, sesame oil, peanut oil, soybean oil, corn oil, propylene glycol or polyethylene glycol and, if necessary, adding disinfectant, stabilizer, tonic agent or analgesic agent.

The pharmaceutical composition of the invention can be administered via a proper route depending on the formulation. The administration mode includes, but is not specifically limited to, internal, external or injection. For injection administration, intravenous, intrmuscular, subcutaneous or intradermal injection is possible.

The amount of the pharmaceutical composition to be administered can properly be determined according to the formulation, the administration route, the purpose of use and the patient's age, weight or symptoms. The amount of the active component in the preparation is, for example, 10 micrograms to 200 milligrams per kilogram weight a day for an adult. Of course, the dosage varies depending on the conditions and the actual dosage may be greater or less than the above range.

The present invention in still further aspect provides a drug conjugate in which the lectin PPA used as a carrier protein for local transport of a drug is bonded with a selective drug for a disease used as an active agent (for example, an anti-cancer drug). The active agent is used for the disease in which the structure of carbohydrates within the cell has modified to N-glycolylneuraminic acid that does not occur in a normal body. Namely, the lectin PPA of the present invention can be used as a carrier protein for local transport of a drug since it can specifically recognize N-glycolylneuraminic acid. The active agent as used herein may be selected from known anti-cancer agents. Examples of cancers include, but not limited to, breast cancer, melanoma or colon cancer.

Hereinafter, the present invention will be described in detail by way of the following examples, which are not intended to limit the scope of the present invention.

EXAMPLE 1

Isolation of Lectin PPA from Korean Marine Crab *Philyra pisum*

Korean marine crabs *Philyra pisum* collected in May through June was washed with distilled water three times. The hemolymph was collected by cutting body and legs. The hemolymph was well mixed with a five-fold dilution of 0.15 M NaCl solution, and then filtered with a 0.2 micrometer syringe filter. Subsequently, the mixture was centrifuged for 5 hours at 4° C. at 100,000×g. The supernatant thus separated was applied onto SEPHADEX (TM) G-25 column. For the column chromatography, 3 grams of SEPHADEX (TM) G-75 were equilibrated by swelling in distilled water (60 milliliters), running through the column to fill 40 milliliters of the gel, and then washing with PBS three times. 1 milliliter of the supernatant obtained by centrifugation of hemolymph was loaded on the column. The resulting chromatogram was made by recording absorbance at 280 nm with a UV/VIS spectrometer. The results are represented in FIG. 1. The results were irrespective of the sex of the crabs.

EXAMPLE 2

Determination of Purity and Molecular Weight of the Lectin PPA

To determine the molecular weight and the purity of the sixth faction (this was identified as lectin PPA by the same methods as Examples 4 and 5) in the chromatogram obtained in Example 1, an electrophoresis analysis was performed on a 12% polyacrylamide gel including 0.1% SDS to compare the molecular weight with standard substances. After the running, the protein band was stained with a coomassie blue reagent. The results are shown in FIG. 2, in which lane 1 is a molecule marker (200, 116, 97, 66, 45, 31, 22.1, 14.4, 6.5 kDa); lane 2 is a stock solution of crab *Philyra pisum*; lane 3 is the isolated lectin PPA of crab *Philyra pisum*; and lane 4 is the isolated lectin PPA of crab *Philyra pisum* (with 2-mercaptoethanol).

Figure 2:
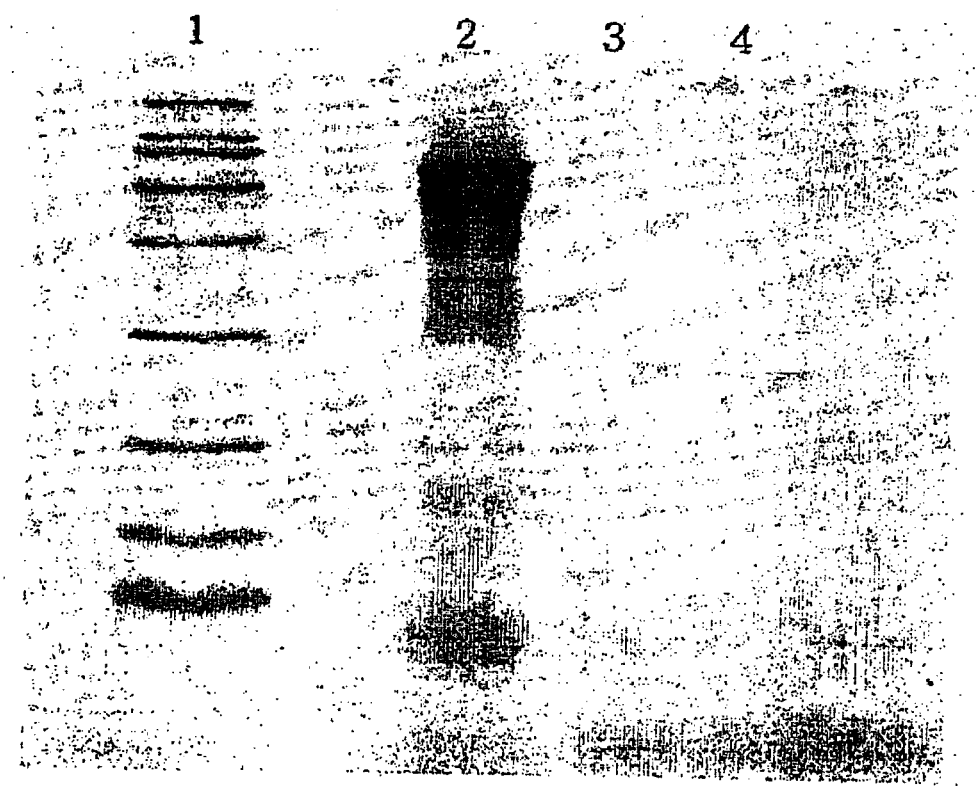
FIG. 2 is a photograph showing an electrophoretic analysis of the lectin PPA prepared by the present invention, in which lane 1 is a molecular weight marker (200, 116, 97, 66, 45, 31, 22.1, 14.4, 6.5 kDa); lane 2 is a stock solution of crab *Philyra pisum*; lane 3 is isolated lectin PPA of crab Philyra pisum; and lane 4 is isolated lectin PPA of crab *Philyra pisum* (with 2-mercaptoethanol).

As can be seen from the results of the electrophoresis in FIG. 2, one band having a molecular weight of about 28.9 kDa was detected in the non-reduced state without addition of 2-mercaptoethanol. A 28.9 kDa band was detected in the reduced state with addition of 2-mercaptoethanol. From the above results, it was confirmed that the PPA is a protein having one subunit and a molecular weight of 28.9 kDa.

EXAMPLE 3

Analysis of N-Terminal Amino Acid of the Lectin PPA

The N-terminal amino acid of the lectin PPA isolated from the Korean marine crab *Philyra pisum* was determined using an amino acid sequencer (Model: Automatic Protein Sequencer, 476A-01-120, Manufacturer: Applied biosystems) according to the manufacturer's instructions. It was revealed that the N-terminal amino acid sequence contains Ile-Val-Gly-Gly-Thr-Glu-Ala-Thr-Pro-His (SEQ ID NO: 1).

EXAMPLE 4

Hemagglutination Assay of the Lectin PPA

Hemagglutination assay was performed using the sixth fraction in the chromatogram obtained in Example 1 by diluting human, dog, mouse, rat and rabbit serums with a 10 millimolar phosphate buffer and 0.15 molar NaCl (pH 7.2) to a concentration of 6.25%. The fractions revealed positive response in the assay were collected and subjected to electrophoresis as shown in FIG. 2 to detect a single band, which was designated as PPA (*Philyra pisum* agglutinin; this lectin component is conveniently referred to as "PPA" in the description and the claims of the present invention). Human blood group (A, B and O type), dog, mouse, rat and rabbit erythrocytes were diluted in the same manner as described above. Each 100 microliters of the erythrocytes was allowed to stand at room temperature together with 100 microliters of the lectin PPA to detect the hemagglutination reaction. As a result, any agglutination was not observed in the human and dog erythrocytes that include only N-acetylneuraminic acid. However, agglutination occurred in the mouse and rat erythrocytes (diluted up to 128-fold) and the rabbit erythrocyte (diluted up to 8-fold) that include N-glycolylneuraminic acid. The results are as shown in Table 1.

TABLE 1

| Erythrocyte | Type of sialic acid | Minimal hemagglutination inhibiting activity |
|---|---|---|
| Human type A | NeuAc | — |
| Human type B | NeuAc | — |
| Human type O | NeuAc | — |
| Dog | NeuAc | — |
| Mouse | NeuGc, NeuAc, O-acetylsialic acid | 128 |
| Rat | NeuAc, NeuGc, O-acetylsialic acid | 128 |
| Rabbit | NeuGc, NeuAc, O-acetylsialic acid | 8 |

Note: The number of minimal hemagglutination inhibiting activity represents the minimal fold dilution obtained by diluting the lectin PPA two-fold against each erythrocyte diluted to 6.25%, where the negative sign (−) means no inhibition from hemagglutination, NeuGc is N-glycolylneuraminic acid, and NeuAc is N-acetylneuraminic acid.

The above results show that the lectin PPA selectively recognizes N-glycolylneuraminic acid only and inhibits agglutination of the lectin PPA up to 128-fold dilution in the mouse and rat erythrocytes, this indicating that the lectin PPA exists at a concentration of about 128 micrograms per milliliter since the above value is the minimum concentration for agglutination in the case where the concentration of the concentrated lectin solution is about 1 microgram per milliliter.

EXAMPLE 5

Hemagglutination-Inhibition Assay of the Lectin PPA

In order to confirm that the lectin PPA of the present invention recognizes N-glycolylneuraminic acid, hemagglutination-inhibition reaction was performed using monosaccharide, disaccharide and glycoprotein. 50 Microliters of a 128-fold diluted solution of lectin PPA in 0.15 molar NaCl and 50 microliters of each of 1 milligram per milliliter solutions of monosaccharides (e.g., β-D-glucose, D-galactose, L-fucose, D-mannose, N-acetylneuraminic acid, N-glycolylneuraminic acid, N-acetyl-D-glucosamine, N-acetyl-D-galactosamine and methyl-α-D-glucopoyranoside), disaccharide (e.g., α-lactose, β-lactose, D-lactose, βgentiobiose, maltose, D-raffinose or D-cellobiose) and glycoprotein (e.g., bovine submaxillary mucin, thyroglobulin, fetuin and asialofetuin) in 0. 15 molar NaCl were added to the each well of a 96-well microplate. After the reaction for one hour or more at room temperature, 50 microliters of the erythrocyte suspended in 0.15 molar NaCl was added to each well and reacted for one hour at room temperature. The results are as shown in Table 2.

TABLE 2

| Division | Carbohydrate | Type of sialic acid | Erythrocyte agglutination inhibition concentration |
|---|---|---|---|
| Monosaccharide | beta.-D-glucose | — | — |
| | D-galactose | — | — |
| | L-fucose | — | — |
| | D-mannose | — | — |
| | N-acetylneuraminic acid | NeuAc | — |
| | N-glycolylneuraminic acid | NeuGc | 0.19 mM |
| | N-acetyl-D-glucosamine | — | — |
| | N-acetyl-D-galactosamine | — | — |

TABLE 2-continued

| Division | Carbohydrate | Type of sialic acid | Erythrocyte agglutination inhibition concentration |
|---|---|---|---|
| | Methyl-α-D-glucopyranoside | — | — |
| Disaccharide | α-lactose | — | — |
| | β-lactose | — | — |
| | D-lactose | — | — |
| | β-gentiobiose | — | — |
| | Maltose | — | — |
| | D-raffinose | — | — |
| | D-cellobiose | — | — |
| Glycoprotein | Bovine submaxillary mucin | NeuGc/ NeuAc/O-acetyl-sialic acid | 1.3 μM |
| | Thyroglobulin | NeuGc | 0.4 μM |
| | Fetuin | NeuAc | — |
| | Asialofetuin | — | — |

As can be seen from the results shown in Table 2, N-glycolylneuraminic acid as a monosaccharide, and bovine submaxillary mucin and thyroglobulin containing N-glycolylneuraminic acid as glycoproteins only inhibited the agglutination, while the other monosaccharides, disaccharides and glycoproteins did not inhibit agglutination.

In Table 2, the minimum hemagglutination-inhibition concentration represents the minimum concentration for the 6.25% mouse erythrocyte which revealed the minimum hemagglutination-inhibition by diluting the lectin PPA to 128-folds that showed minimum agglutination and diluting 2-folds each of 100 mM monosaccharide/disaccharide and 100 micromolar glycoprotein. The negative sign (−) means that there is no hemagglutination-inhibition for 100 millimolar monosaccharide/disaccharide and 100 micromolar glucoprotein. NeuGc and NeuAc represent N-glycolylneuraminic acid and N-acetylneuraminic acid, respectively.

EXAMPLE 6

Hemagglutination Inhibition Assay of the Lectin PPA by ELISA

Figure 3:
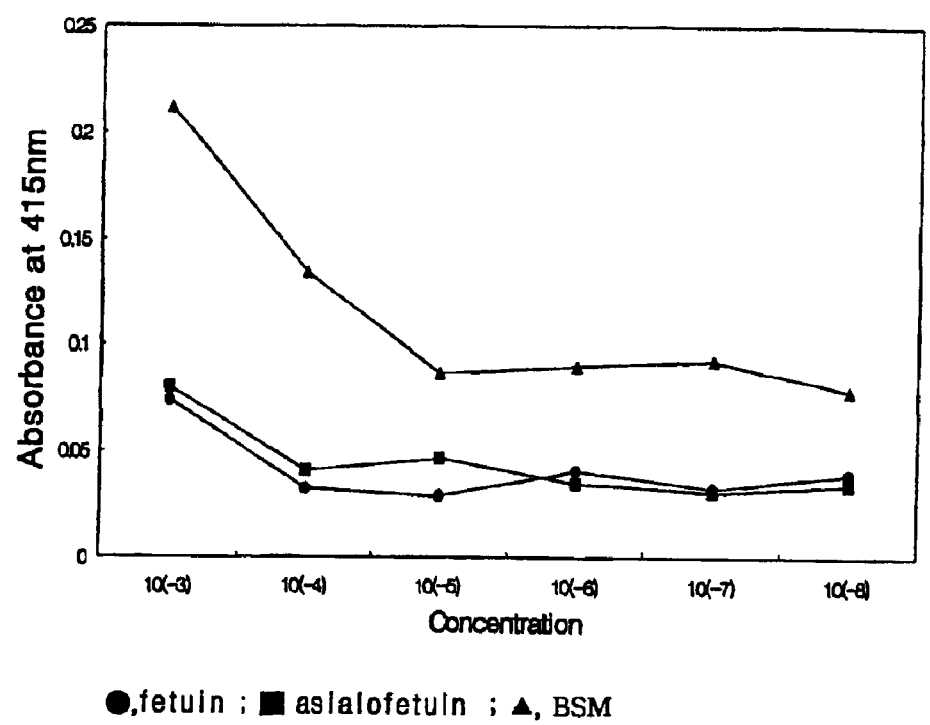
FIG. 3 is a graph showing the results of an ELISA (Enzyme-Linked Immunosorbent Assay) of the lectin PPA prepared by the present invention (circle: fetuin; square: asialofetuin; and triangle: BSM).

In order to more accurately verify the hemagglutination-inhibition reaction of the lectin PPA, ELISA was conducted. Specifically, the lectin PPA bound to a horse radish peroxidase (HRP) was used in examining the reactivity and sensitivity against glycoproteins by ELISA. First, 5.03 milligrams of HRP were dissolved in 0.2 milliliter of a 1.25% glutaraldehyde (EM grade)-100 millimolar sodium phosphate buffer (pH 6.8) and allowed to stand for 18 hours at room temperature. Then, 20 microliters of glycerol and 20 microliters of xylene cyanol were added thereto and this was used in performing gel filtration with a SEPHADEX (TM) G-75 column equilibrated with a 100 millimolar phosphate buffer and 0.15 molar NaCl (pH 7.2). After applying the glutaraldehyde-treated HRP onto the column and eluting with 0.15 molar NaCl, about 1 milliliter of the brownish fraction containing HRP solution was collected. This fraction was dialyzed with a 100 millimolar sodium carbonate-sodium bicarbonate buffer solution (pH 9.5) containing sucrose and followed by the same buffer without sucrose. To 300 microliters of HRP thus obtained were added 150 microliters of lectin PPA (concentration of about 0.4 milligram per milliliter concentration) containing with 0.15 molar NaCl. After confirming the pH value 9.0 or more, the resultant solution was incubated for 24 hours at 4° C. to prepare peroxidase-labeled lectin PPA. In the mean time, 1 milligram of each of fetuin, asialofetuin and bovine submaxillary mucin was dissolved in 1 milliliter of PBS and serial 10-fold dilutions were made. Each 100 microliters of the $10^3$ to $10^8$-fold diluted solutions was then coated on each well of a 96-well microplate and reacted for 1 hour at 37° C. After removing the coated solution by aspiration, each well was washed with 100 microliters of PBS and 0.1% Tween 20 (PBST) three times and reacted with 100 microliters of PBS containing 1% BSA as a blocking solution for 1 hour at 37° C. The reaction solution was removed by aspiration and each well was washed with 100 microliters of PBST three times. To each well were added 100 microliters of the peroxidase-labeled PPA and the solution was reacted for 1 hour at 37° C. After removing the coated solution by aspiration, each well was washed with 100 microliters of PBST five times. Each 100 microliters of the solution prepared by adding 5 microliters of $H_2O_2$ to 5 milliliters of ABTS in PBS was added to each well. Then, the absorbance at 415 nanometers of each well was measured with a microplate reader. To eliminate the error of each well caused by the time difference while adding ABTS, a second measurement was performed after 10 minutes to determine the difference in the absorbances between the time of 10 minutes and 0 minute. The results are shown in FIG. 3. As can be seen from FIG. 3, when each 1 miligram per milliliter solution of fetuin, asialofetuin and bovine submaxillary mucin solution was diluted to $10^3$ to $10^8$-fold, no response occurred in the fetuin and asialofetuin samples which do not contain N-glycolylneuraminic acid. However, a response in which absorbance value is increased was observed in the $10^3$-fold diluted BSM solution in which N-glycolylneuraminic acid is bound. The absorbance was decreased with the lowering of the concentration. This result supports the use of the lectin PPA of the present invention as a diagnosing agent or a carrier protein.

EXAMPLE 7

Anti-Proliferation Effect of Lectin PPA on Cancer Cell

The anti-proliferation effect of the lectin PPA on cancer cells was evaluated using MTT (3-[4,5-dimethyldiazol-2-yl]-2,5-diphenyl tetrazolium bromide) assay (See Mosmann T et al., J. Immunol. Methods 65, pp 55–63 (1983)). Each cancer cell was cultured in a 90% RPMI 1640-10% FBS (fatal bovine serum) medium. Using a hematocytometer, the number of cells was determined as about $1\times10^4$ per 100 microliters. Then, the sample was added to the wells of a 96-well microplate. After addition of 100 microliters of 1 micromolar lectin PPA, the plate was allowed to stand for 72 hours in an incubator maintaining 5% $CO_2$. To each well were added 50 microliters of the MTT reagent and the mixture was allowed to stand for 4 hours in the $CO_2$ incubator. After discarding the supernatant and adding 150 microliters of dimethyl sulfoxide, the sample solution was mixed for 10 minuutes and measured the absorbance at 540 nanometers with the microplate reader. As a control, the same experimental procedure was performed under the above conditions without adding the lectin PPA. The percentage of proliferation was designated as 100% for the control and the relatively decreased percentage of proliferation for the samples containing the lectin PPA was compared to the control. The same procedures were repeated three times to express the decreased percentage as average value +standard deviation. As can be seen from the results of Table 3, 1 micromolar lectin PPA showed anti-proliferation effects of 15.9±2.9% for human hepatoma cell Hep3B, 8.8±2.2% for human bladder cancer cell T24, 32.5±2.5% for human lung cancer cell A549, 21.9±4.8% for human stomach cancer cell SNU-C1 and 18.6±1.8% for human colon cancer cell SNU-1 (all of the cell lines as used herein were purchased from the Korean Cell Line Bank (KCLB)).

TABLE 3

| Origin of cancer cell | Name of cancer | Composition of medium | Anti-proliferation % |
|---|---|---|---|
| Human hepatoma | Hep3B | RPMI 1640 90%, FBS 10% | 15.9 ± 2.9% |
| Human bladder cancer | T24 | RPMI 1640 90%, FBS 10% | 8.8 ± 2.2% |
| Human lung cancer | A549 | RPMI 1640 90%, FBS 10% | 32.5 ± 2.5% |
| Human stomach cancer | SNU-C1 | RPMI 1640 90%, FBS 10% | 21.9 ± 4.8% |
| Human colon cancer | SNU-1 | RPMI 1640 90%, FBS 10% | 18.6 ± 18% |

EXAMPLE 8

| Pharmaceutical Preparation Type of preparation (tablet) | |
|---|---|
| Active component (lectin PPA) | 10 mg |
| Lactose | 80 mg |
| Starch | 17 mg |
| Magnesium stearate | 3 mg |
| Crystalline cellulose | 10 mg |

The tablets were prepared by the conventional method so as to contain the above-mentioned ingredients per tablet. If necessary, the tablets may additionally include an enteric coating (e.g., hydroxypropylmethylcellulose phthalate), a sugar coating or a film (e.g., ethyl cellulose).

INDUSTRIAL APPLICABILITY

The lectin PPA prepared by the present invention which specifically recognizes N-glycolylneuraminic acid can be used as a diagnostic agent based on the principle that it specifically recognizes N-glycolylneuraminic acid which does not occur on normal cells but specifically expressed on breast cancer, melanoma or colon cancer cells. The lectin PPA can also be used as a carrier protein for local transport of a selective drug, in which the side effect is minimized by conjugating lectin with anti-cancer agents for breast cancer, melanoma and colon cancer, etc. In addition, since the lectin PPA has various beneficial biochemical characteristics, it can also be used as an anti-proliferation agent for cancer cells of hepatoma, bladder cancer, lung cancer, stomach cancer and colon cancer.

What is claimed is:

1. A lectin PPA extracted from the hemolymph of Korean marine crab *Philyra pisum* which is characterized in that it is a single subunit having a molecular weight of 28.9 kDa and its N-terminal amino acid sequence is represented in sequence no. 1 of the sequence listing.

2. The PPA protein as claimed in claim 1, wherein it binds to N-glycolylneuraminic acid or a glycoprotein including N-glycolylneuraminic acid by hemagglutination reaction, hemagglutination-inhibition reaction or enzyme-linked immunosorbent assay (ELISA).

3. A process for preparing a lectin PPA protein from the hemolymph of Korean marine crab *Philyra pisum*, which comprising the steps of: diluting the hemolymph of *Philyra pisum* with NaCl, filtering the precipitate off and centrifuging the resulting solution to isolate a supernatant; and applying the supernatnat onto a Sephadex G-25 column or onto an affinity column prepared by binding bovin submaxillary mucin or thyroglobulin and an affinity column-manufacturing material to isolate the PPA protein.

4. A diagnosing agent for a disease in which the structure of carbohydrates within the cells is modified to N-glycolylneuraminic acid that does not exist in normal body, which comprises the lectin PPA.

5. The diagnosing agent as claimed in claim 4, wherein the disease is a cancer.

6. A drug conjugate in which the lectin PPA protein according to claim 1 as a carrier protein for local transport of a drug and a selective drug as an active agent are bonded.

7. The drug conjugate as claimed in claim 6, wherein the active agent is a drug for treatment of a disease in which the structure of carbohydrates within the cell is modified to N-glycolylneuraminic acid that does not exist in a normal body.

8. The drug conjugate as claimed in claim 6, wherein the disease is a cancer.

9. The drug conjugate as claimed in claim 8, wherein the disease includes breast cancer, melanoma and colon and rectal cancer.

10. An anti-proliferation agent for cancer cells comprising the lectin PPA protein according to claim 1 as an active agent.

11. The anti-proliferation agent for cancer cells as claimed in claim 10, wherein the cancer includes hepatoma, bladder cancer, stomach cancer and colon and rectal cancer.

* * * * *